United States Patent
Tajima

(10) Patent No.: US 10,335,526 B2
(45) Date of Patent: Jul. 2, 2019

(54) DETACHABLE PERCUTANEOUS CONNECTOR

(71) Applicant: HeartWare, Inc., Miami Lakes, FL (US)

(72) Inventor: Michael Tajima, Acton, MA (US)

(73) Assignee: HeartWare, Inc., Miami Lakes, FL (US)

( * ) Notice: Subject to any disclaimer, the term of this patent is extended or adjusted under 35 U.S.C. 154(b) by 3 days.

(21) Appl. No.: 15/621,267

(22) Filed: Jun. 13, 2017

(65) Prior Publication Data

US 2017/0354772 A1     Dec. 14, 2017

Related U.S. Application Data

(60) Provisional application No. 62/349,242, filed on Jun. 13, 2016.

(51) Int. Cl.
*A61M 1/10*     (2006.01)
*A61M 1/12*     (2006.01)
(Continued)

(52) U.S. Cl.
CPC ......... *A61M 1/1008* (2014.02); *A61F 15/008* (2013.01); *A61M 1/127* (2013.01);
(Continued)

(58) Field of Classification Search
CPC ...... A61M 2205/04; A61M 2205/8262; A61M 1/127; A61M 39/02; A61M 2039/0288;
(Continued)

(56) References Cited

U.S. PATENT DOCUMENTS 5,904,646 A * 5/1999 Jarvik ............... A61M 39/0247
                                                            600/16
7,044,911 B2     5/2006 Drinan et al.
(Continued)

FOREIGN PATENT DOCUMENTS

EP      1344539 A2 * 9/2003 .............. A61M 1/12
WO     9934754 A1     7/1999
WO     2015063272 A1  5/2015

OTHER PUBLICATIONS

International Search Report and Written Opinion dated Sep. 20, 2017, for corresponding International Application No. PCT/US2017/037168 filed on Jul. 6, 2017, 10 pages.

*Primary Examiner* — Catherine M Voorhees
(74) *Attorney, Agent, or Firm* — Christopher & Weisberg, P.A.

(57) ABSTRACT

A cover for a percutaneous connector extending through the skin of a patient. The cover includes a structure having an inner side and an outer side. A first separable connector is mounted to the structure and disposed entirely within the structure, the first separable connector being configured to detachably engage and electrically connect with the percutaneous connector. A second separable connector is mounted to the structure and electrically connected to the first separable connector, the second separable connector being exposed at the outer side of the structure and being configured to detachably engage and electrically connect with an external device. The inner side of the structure defines a skin-engaging surface at least partially surrounding the first separable connector and the percutaneous connector, when the first separable connector is engaged with the percutaneous connector.

19 Claims, 9 Drawing Sheets

(51) Int. Cl.
*A61F 15/00* (2006.01)
*A61M 39/02* (2006.01)

(52) U.S. Cl.
CPC . *A61M 39/0247* (2013.01); *A61M 2039/0267* (2013.01); *A61M 2039/0288* (2013.01)

(58) Field of Classification Search
CPC .......... A61M 1/008; A61M 2039/0267; A61M 39/0247; A61F 2/28; A61F 2/0774; A61F 15/008
See application file for complete search history.

(56) References Cited

U.S. PATENT DOCUMENTS

| | | | |
|---|---|---|---|
| 2010/0063347 A1 | 3/2010 | Yomtov et al. | |
| 2011/0071336 A1 | 3/2011 | Yomtov et al. | |
| 2012/0130315 A1 | 5/2012 | Weadock et al. | |
| 2013/0237840 A1 | 9/2013 | Warren et al. | |
| 2014/0275727 A1 | 9/2014 | Bonde et al. | |
| 2015/0083122 A1* | 3/2015 | Velez-Rivera | A61M 16/0816 128/202.22 |
| 2015/0364863 A1* | 12/2015 | Andrus | A61M 1/127 439/39 |
| 2016/0175502 A1 | 6/2016 | McSweeney et al. | |

\* cited by examiner

DETACHABLE PERCUTANEOUS CONNECTOR

CROSS-REFERENCE TO RELATED APPLICATION

This application is related to and claims priority to U.S. Provisional Patent Application Ser. No. 62/349,242, filed Jun. 13, 2016, entitled DETACHABLE PERCUTANEOUS CONNECTOR, the entirety of which is incorporated herein by reference.

STATEMENT REGARDING FEDERALLY SPONSORED RESEARCH OR DEVELOPMENT n/a

TECHNICAL FIELD

The present invention relates to a method and system for attaching and detaching an external device from a percutaneous connector.

BACKGROUND

A mechanical circulatory support device or "MCSD," also referred to as a ventricular assist device or "VAD," typically includes a pump implanted in the patient and connected in fluid communication with the patient's circulatory system. The pump assists the pumping action of the patient's heart. MCSD's typically use an external power source and an external controller to ensure proper operation of the heart pump. Since the power source and the controller are external to the implant, an electrical connection across the boundary of a patient's skin is required. This is typically achieved by providing a percutaneous cable that serves as an interface connecting the external device to the internal implant. The percutaneous cable extends through the skin and provides a detachable connection to the external device. MCSD's typically require constant power to ensure continuous pump support. Since all electronics are external to the body, they require uninterrupted attachment to bulky external electronics that are a physical burden to patients.

It has been proposed to provide MCSD's with an internal battery and a controller that can maintain the pump in operation for short intervals when the external device is disconnected as, for example, while the patient is bathing or getting dressed. This concept could utilize a detachable connector coupling the external power sources and the internal electronics. The detachable connector should provide a secure electrical connection, and should allow the patient to remove the detachable connector without causing pain or injury.

The skin breach caused by a percutaneous connector or cable extending outwardly from the skin can create an area of vulnerability for infections. If the patient repeatedly makes and breaks the connection, this process can impose mechanical stress on the percutaneous connector or cable and the surrounding tissues, and can expose the skin breach to microbes. Moreover, mechanical stress may be applied by accident as, for example, if a cable attached to the external device is accidently pulled. Accordingly, further improvement would be desirable.

SUMMARY

The present invention advantageously provides for a cover for a percutaneous connector extending through the skin of a patient. The cover includes a structure having an inner side and an outer side. A first separable connector is mounted to the structure and disposed entirely within the structure, the first separable connector being configured to detachably engage and electrically connect with the percutaneous connector. A second separable connector is mounted to the structure and electrically connected to the first separable connector, the second separable connector being exposed at the outer side of the structure and being configured to detachably engage and electrically connect with an external device. The inner side of the structure defines a skin-engaging surface at least partially surrounding the first separable connector and the percutaneous connector, when the first separable connector is engaged with the percutaneous connector.

In another aspect of this embodiment, the skin-engaging surface extends entirely around the first separable connector.

In another aspect of this embodiment, the cover includes an adhesive on the skin-engaging surface.

In another aspect of this embodiment, the structure includes a housing and a flexible base extending beyond a periphery of the housing, the flexible base defining at least a portion of the skin-engaging surface.

In another aspect of this embodiment, the base is integral with the housing.

In another aspect of this embodiment, the second separable connector is disposed in a second housing and connected to the first separable connector by an electrical conduit, the second separable connector being accessible to connect with an external device and manipulation of the second separable connector does not interfere with the connection between the first separable connector and the percutaneous connector when the cover is disposed over the first separable connector and the first separable connector is engage with the percutaneous connector.

In another aspect of this embodiment, the cover includes a closure configured to releasably engage at least one of the structure and the second separable connector, the closure being configured to cover the second separable connector when the external device connection is absent.

In another aspect of this embodiment, the cover includes an alarm mounted to the structure and electrically connected to at least one from the group consisting of the first separable connection and the second separable connector, the alarm being configuration to emit an alarm signal responsive to an electrical condition prevailing at the at least one from the group consisting of the first separable connection and the second separable connector.

In another aspect of this embodiment, the alarm signal includes at least one from the group consisting of an audio, tactile, and visual alarm.

In another embodiment, a method of providing a connection between an external device and an internal device implanted in a patient and electrically connected through a percutaneous connection element across a skin surface of the patient includes coupling a first separable connector to the to the percutaneous connection element. The first separable connector is secured to the skin surface independent of the engagement between the first separable connector and the percutaneous connection element, the first separable connector being electrical connected to a second separable exposed outside of the patient. The external device is connected to the second separable connector.

In another aspect of this embodiment, the method includes detaching the external device from the second separable connector.

In another aspect of this embodiment, the method includes removing the first and second separable connectors.

In another aspect of this embodiment, securing the first separable connector includes applying an adhesive-bearing element to the skin of the patient, and wherein the adhesive-bearing element holds the first separable connector in place.

In another aspect of this embodiment, the percutaneous connection element is a percutaneous connector extending through the skin, and wherein application of the adhesive-bearing element covers the percutaneous connector and protects the percutaneous connector from microbes.

In another aspect of this embodiment, applying the adhesive-bearing element includes applying a cover including the first separable connector and the adhesive-bearing element.

In another aspect of this embodiment, the method includes operating an alarm circuit mounted to the cover and electrically connected to at least one of from the group consisting of the first separable connector and the second separable connection, the alarm circuit being configured to detect an electrical condition representing a condition of the internal device and emit an alarm signal responsive to such condition.

In another aspect of this embodiment, the percutaneous connection element is a percutaneous cable extending through the skin surface of the patient.

In another aspect of this embodiment, the first separable connector is secured to the skin remote from a skin breach location where the percutaneous cable extends through the skin.

In yet another embodiment, a cover for a percutaneous connector extending through the skin of includes a housing defining a substantially dome shape and a base surrounding the housing and extending beyond the periphery of the housing. A first separable connector is mounted to the structure and disposed entirely within the structure. The first separable connector is configured to detachably engage and electrically connect with the percutaneous connector. A second separable connector is mounted to the dome and electrically connected to the first separable connector, the second separable connector being exposed at the outer side of the dome and being configured to detachably engage and electrically connect with an external device. The inner side of the base defining a skin-engaging surface surrounding and enclosing the first separable connector and the percutaneous connector when the first separable connector is engaged with the percutaneous connector, the inner side including an adhesive on the skin-engaging surface.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 3:
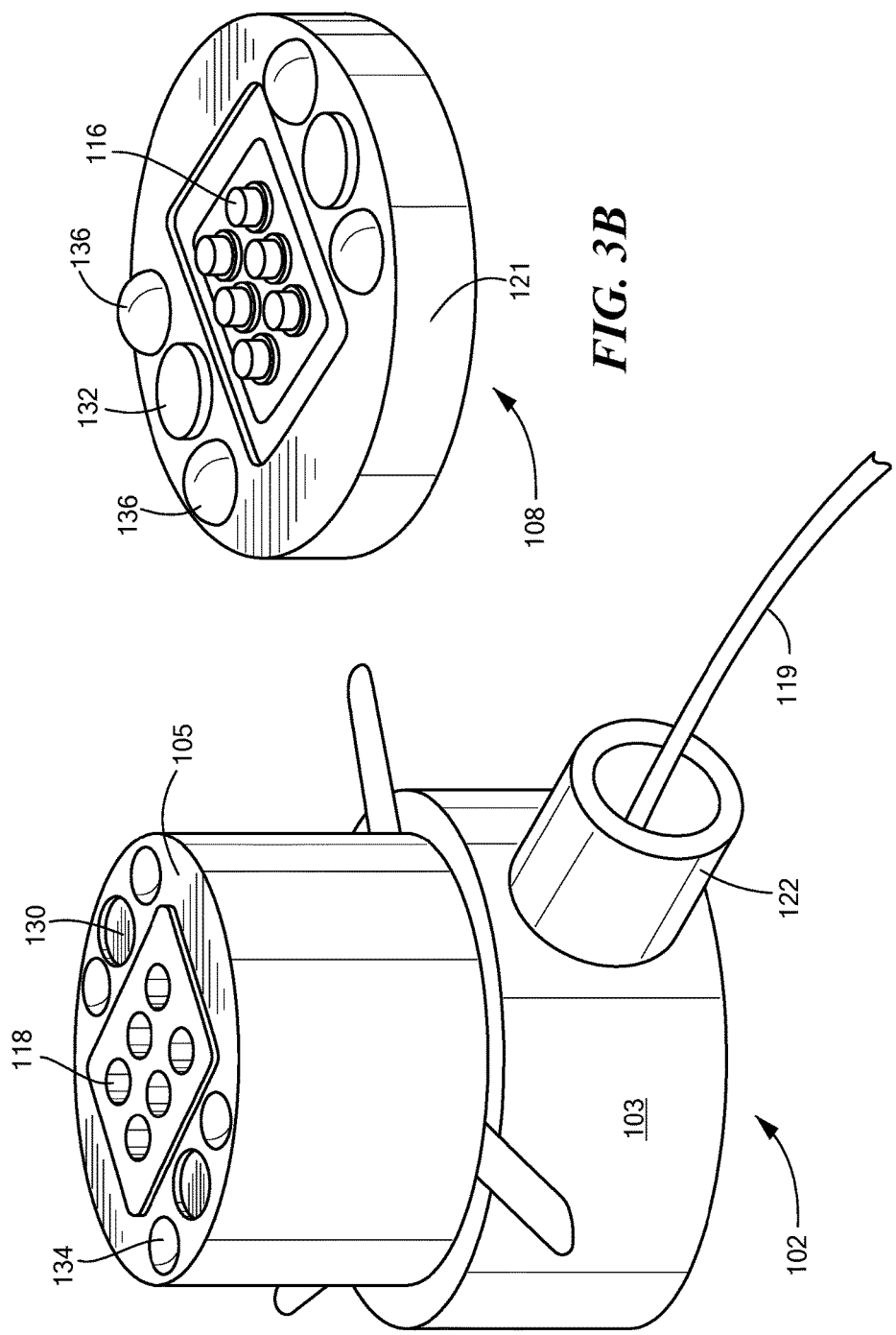
FIG. 3A is a perspective view of a percutaneous connector.
FIG. 3B is a perspective view of a separable connector adapted for engagement with the percutaneous connector of FIG. 3A.

Referring now to the drawings in which like reference designators refer to like element, there is shown in FIG. 3A a perspective view of a percutaneous connector 102. Percutaneous connector 102 includes a body having an internal portion 103 adapted for implantation within a patient, beneath the skin surface, and an external portion 105 that is exposed at or above the skin surface when the internal portion is implanted. The external portion includes a set of six electrical contacts 118, each having a concave surface. The contacts are embedded in a mass of electrically insulating material that is fixed to the body of the percutaneous connector. Each contact 118 is electrically connected to a separate electrical conductor (not shown) within a cable 119, schematically indicated in FIG. 3A. Cable 119 extends from an internal portion 122 of the percutaneous connector body. The percutaneous connector has one or more magnets 130 mounted to the external portion 105 of the percutaneous connector body. Hemispherical recesses 134 are provided in the connector body.

A first separable connector 108, also referred to herein as the "inner" separable connector, (FIG. 3B) has a body 121 and contacts 116 mounted to body 121 in a pattern corresponding to the pattern of the contacts 118 of percutaneous connector 102 (FIG. 3A). Each contact 116 of the first separable connector 108 includes a pin adapted to engage in the recess of the corresponding contact 118 of the percutaneous connector 102. The first separable connector 108 also includes hemispherical cam members 136 on body 121 arranged in a pattern corresponding to the pattern of the recesses 134 in the body of the percutaneous connector 102. Magnets 132 are mounted to body 121. The first separable connector 108 can be mated with the percutaneous connector 102 by juxtaposing body 121 with the external portion 105 of the percutaneous connector body. Mutual attraction between the magnets of the first separable connector and the magnets of the percutaneous connector urges the connectors into alignment with one another so that the cam members 136 of the first separable connector are aligned with the recesses 134 of the percutaneous connector. In this condition, each contact 116 of the first separable connector is aligned with the corresponding contact 118 of the percutaneous connector. The magnetic attraction pulls the bodies of the connectors toward one another, and thus forces the contacts 116 and 118 into engagement with one another. The features of the percutaneous connector and the first separable connector discussed above may be as described in U.S. Published Patent Application No. 2015/0364863 ("the '863 Publication"), the disclosure of which is hereby incorporated by reference herein. As further described in the '863 Publication, the contacts of the first separable connector may include spring-biased pins or other elements that facilitate reliable contact with the mating contacts of the percutaneous connector despite small misalignments or tilting of one connector relative to the other.

Figure 1:
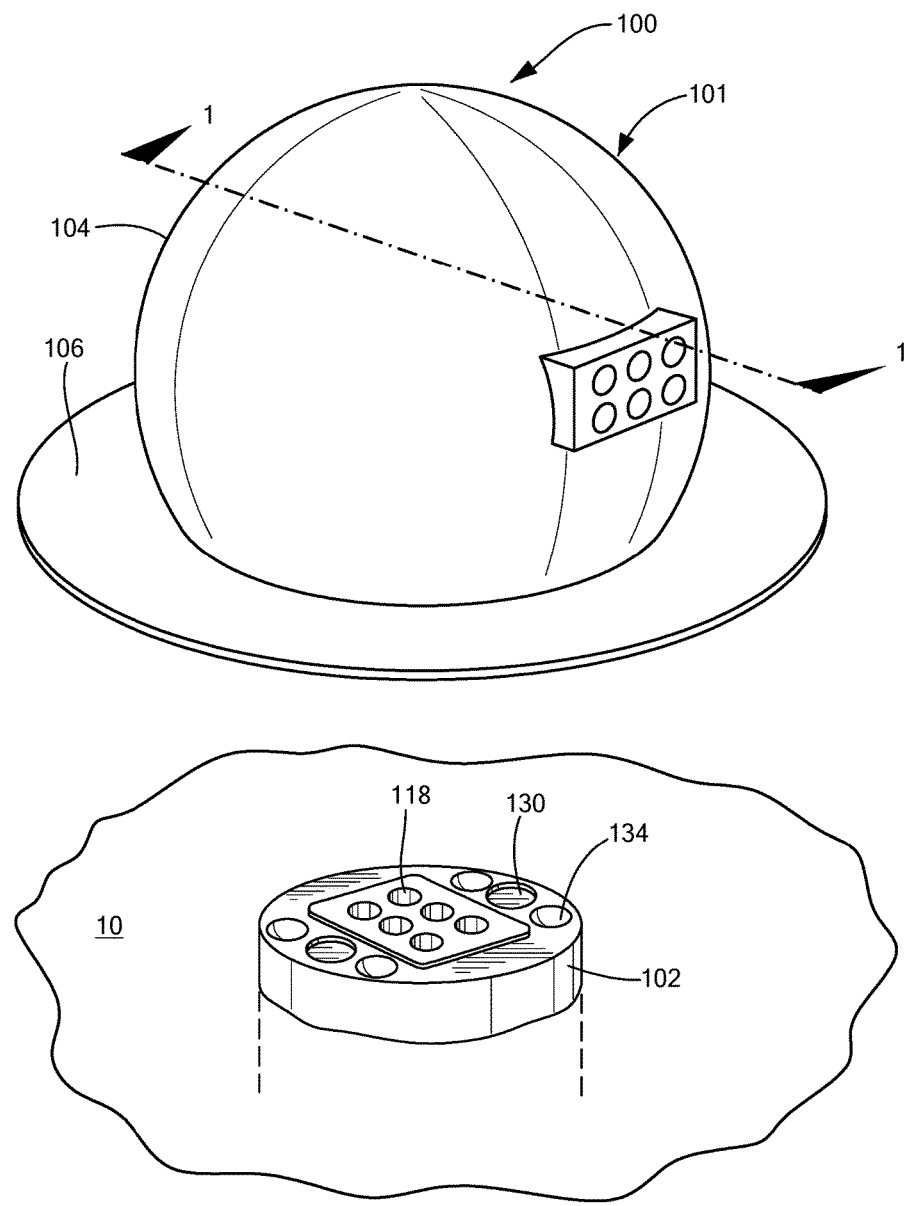
FIG. 1 is a diagrammatic perspective view of a cover according to one embodiment of the present disclosure in conjunction with a percutaneous connector.
Figure 2:
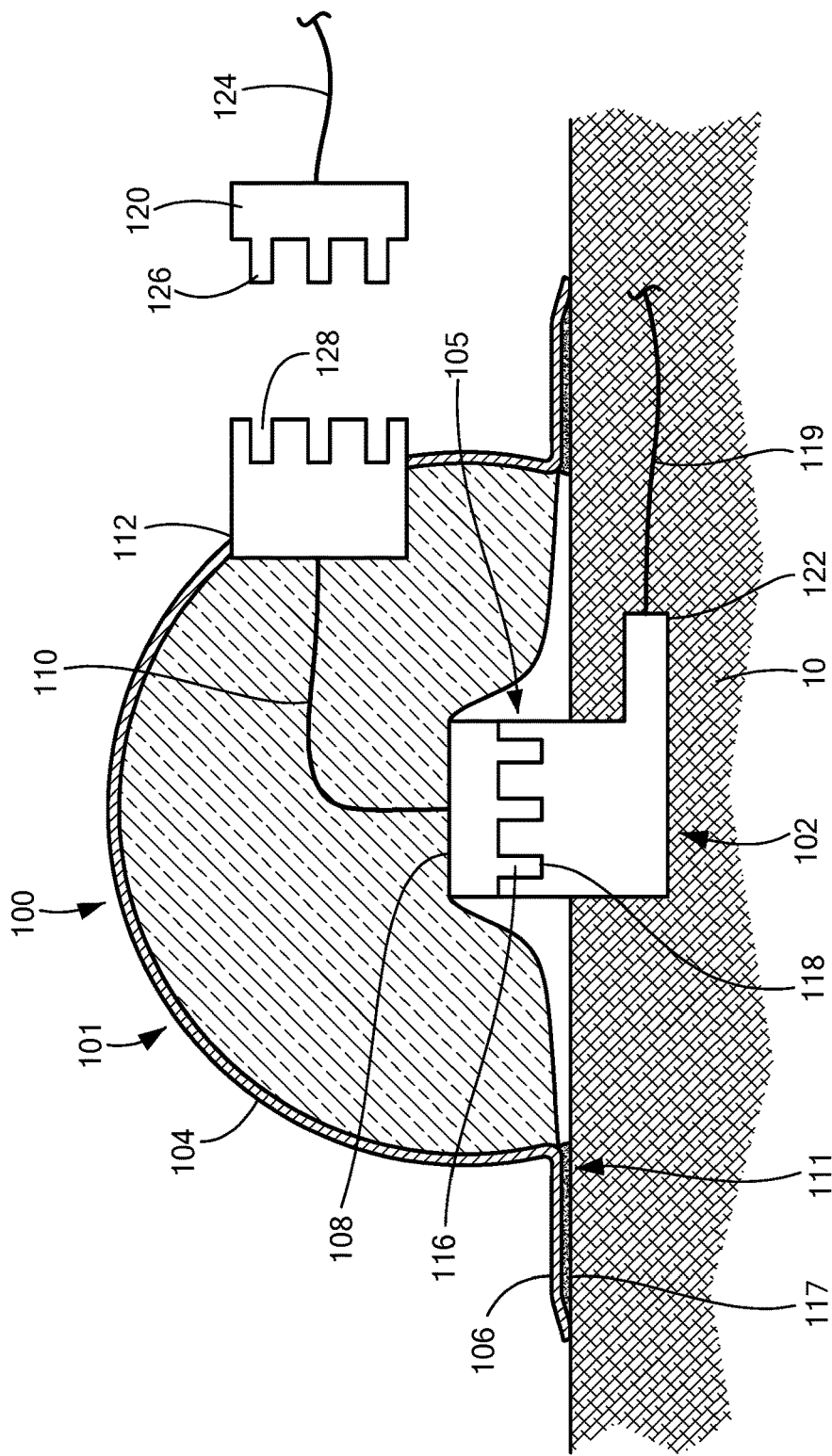
FIG. 2 is a diagrammatic cross-sectional view along the center line 1-1 of the cover of FIG. 1.

Now referring to FIGS. 1 and 2, a cover 100 includes a structure incorporating a generally dome-shaped central housing 104 and a base 106 encircling the housing. The structure has an outer side 101 visible in the perspective view of FIG. 1 and an inner side 111 that faces downwardly as seen in the sectional view of FIG. 2. In this embodiment, the base 106 and central housing 104 are formed integrally with one another. For example, the base and housing may be formed as a single piece of a polymer suitable for skin contact. Base 106 is flexible, and defines a skin-engaging surface on the inner side 111 of the structure. The skin-engaging surface of the base 106 carries a layer of an adhesive 117 suitable for making a peelable adhesive bond with the skin 10 of a patient. For example, adhesive 117 may be an adhesive of the type used in bandages and surgical dressings. In other embodiments, the skin-engaging surface may not have a flexible base extending around the central housing structure, and the skin-engaging surface may be attached to the skin 10 by using an adhesive sheet overlying the cover or by other mechanical or magnetic means. As best seen in FIG. 2, the first or inner separable connector 108 (FIG. 3B) is mounted to the structure of cover 100 so that at least the features of connector 108 adapted to mate with the percutaneous connector are exposed at the inner side 111 of the structure. In this embodiment, the body of connector 108 is embedded in the central housing, with features such as the contacts 116 and the cams 136 (FIG. 3B) exposed at the inner surface. Base 106 surrounds the first separable connector 108.

A second separable connector 112, also referred to herein as the "outer" separable connector, is also mounted to the structure. In this embodiment, the second or outer separable connector 112 has contacts 128 and other mating features identical to the mating features of percutaneous connector 102. Each contact 128 of the second separable connector 112 is electrically connected to a corresponding contact 116 of the first separable connector by a wire incorporated in a cable 110 extending within the housing 104. The mating features of the second separable connector are exposed at the outer side of the structure. The cover, including the first and second separable connectors and the electrical connection between the connectors, desirably provide a seal against passage of contaminants and microorganisms from the outer side 101 to the inner side around or through the connectors. For example, the material forming the structure of cover 100 may be in sealing engagement with the bodies of connectors 108 and 112, with cable 110, or both. Such sealing engagement may be provided, for example, by molding the material of the cover around the connector bodies and cable.

Figure 7:
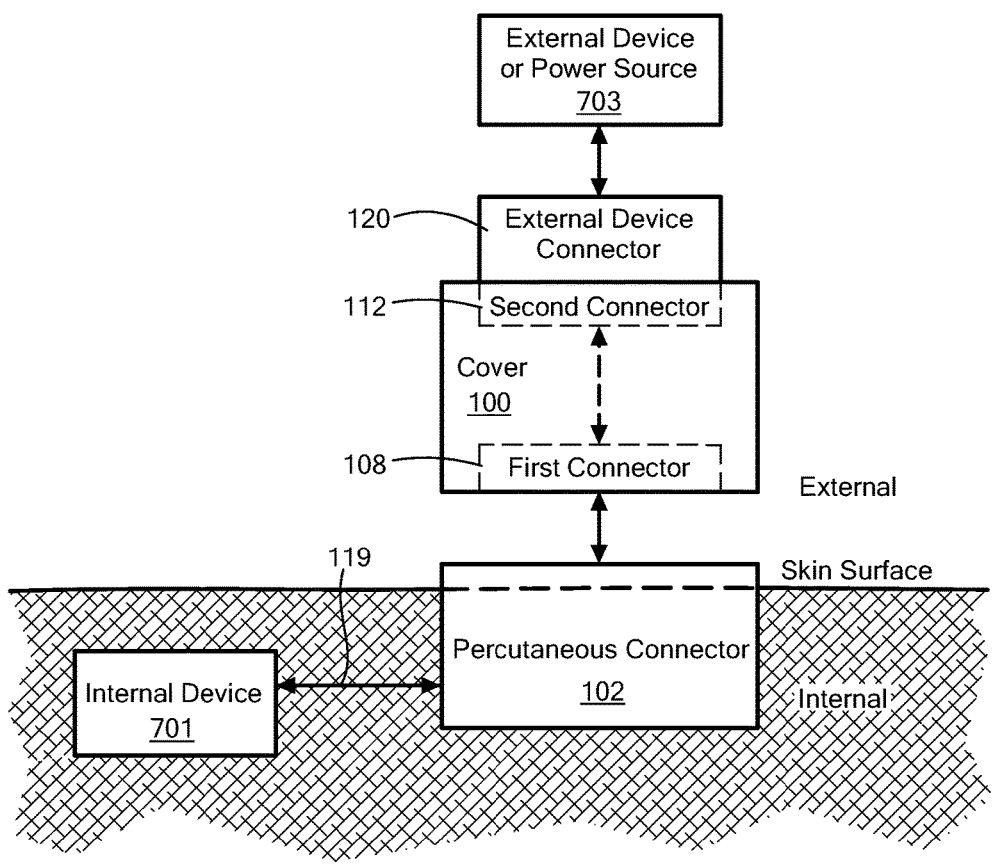
FIG. 7 is a schematic drawing of a circuit between an internal device and external device connected through a percutaneous connector.

In a method according to a further aspect of the present disclosure, the cover 100 is used to provide protection to a percutaneous connector 102 that has previously been implanted in the patient and electrically connected to an internal device 701 by the implanted cable 119, as schematically depicted in FIG. 7. The skin surface of the patient surrounding the percutaneous connector desirably is cleaned and sanitized. Cover 100 is placed over the external portion 105 of the percutaneous connector, and the first separable connector 108 of the cover is coupled to the percutaneous connector 102 so that the contacts 116 of connector 108 are engaged with the percutaneous connector. The skin-engaging surface defined by the base 106 of the cover is secured on the adjacent skin by the adhesive layer 117 to seal the cover 100 around the percutaneous connector 102. The cover 100 forms a 360-degree seal around the skin breach at the percutaneous connector. Attaching the cover to the skin by the adhesive layer 117 also secures the first or inner separable connector 108 to the percutaneous connector 102 independently of engagement between the first separable connector and the percutaneous connector. Thus, the cover helps to secure the first separable connector 108 in engagement with the percutaneous connector 102, thereby maintaining a secure electrical connection between these connectors.

The second or outer separable connector 112 is electrically connected through the first or inner separable connector 116 to the percutaneous connector. Thus, an external device 703 (FIG. 7) can be electrically connected to the internal device 701 by coupling a connector 120 (FIGS. 2, 7) associated with the external device connector to the second separable connector 112. This establishes a secure and detachable connection between the implanted internal device and the external device. When the patient needs to detach the external device during activities such as showering or swimming, the patient can detach the external device by removing the external device connector 120 from the second separable connector 112. Reconnecting to the external device will only require the patient to reattach the external device to the second separable connector. The cover 100, which completely encloses the percutaneous connector even when the external device is unconnected, ensures that attaching and reattaching the external device does not expose the vulnerable skin breach area to harmful organisms and foreign bodies. Moreover, the mechanical connection between the cover 100 and the skin helps to assure that the first separable connector 108 and the percutaneous connector 102 are protected against mechanical loads applied during connection and disconnection of the external device connector. The cover also protects the first separable connector and the percutaneous connector against accidental mechanical loads. For example, if the cable connecting the external device connector and the external device housing is accidently pulled as, for example, by dropping the external device housing or snagging the cable in clothing. The protection against mechanical loads helps to prevent damage to the interface between the percutaneous connector and surrounding tissues, and thus helps to promote healing at the skin breach.

The cover 100 can be removed from the patient by peeling the adhesive 117 from the skin and disconnecting the first separable connector from the percutaneous connector. The cover can then be replaced with a new cover or with the same cover, and the external device can be reconnected. Typically, removal and replacement of the cover are carried out under controlled, sanitary conditions either by the patient or by trained medical personnel. The skin surrounding the percutaneous connector is typically sanitized while the cover is absent. Desirably, the cover is inexpensive enough that the cover can be replaced with a new cover each time that it is removed.

As mentioned above, the second connector 112 in this embodiment has mating features similar to the corresponding features of the percutaneous connector. The external device connector 120 has mating features similar to the mating features of the first connector 108, namely, contacts 126 configured to mate with contacts 128 of the second connector 112, and a cable 124 configured to connect to external device 703. Thus, the external device connector can be engaged directly with the percutaneous connector 102 if the cover 100 is absent. This arrangement is particularly advantageous for use with existing devices that were originally intended for direct engagement between the external device connector and the percutaneous connector. There is no need to modify the percutaneous connector in order to use the cover. As discussed in greater detail in the '863 Publication, the particular connector design used in this embodiment allows the mated connections to be separated from one another by a mechanical load above a predetermined threshold.

Figure 4:
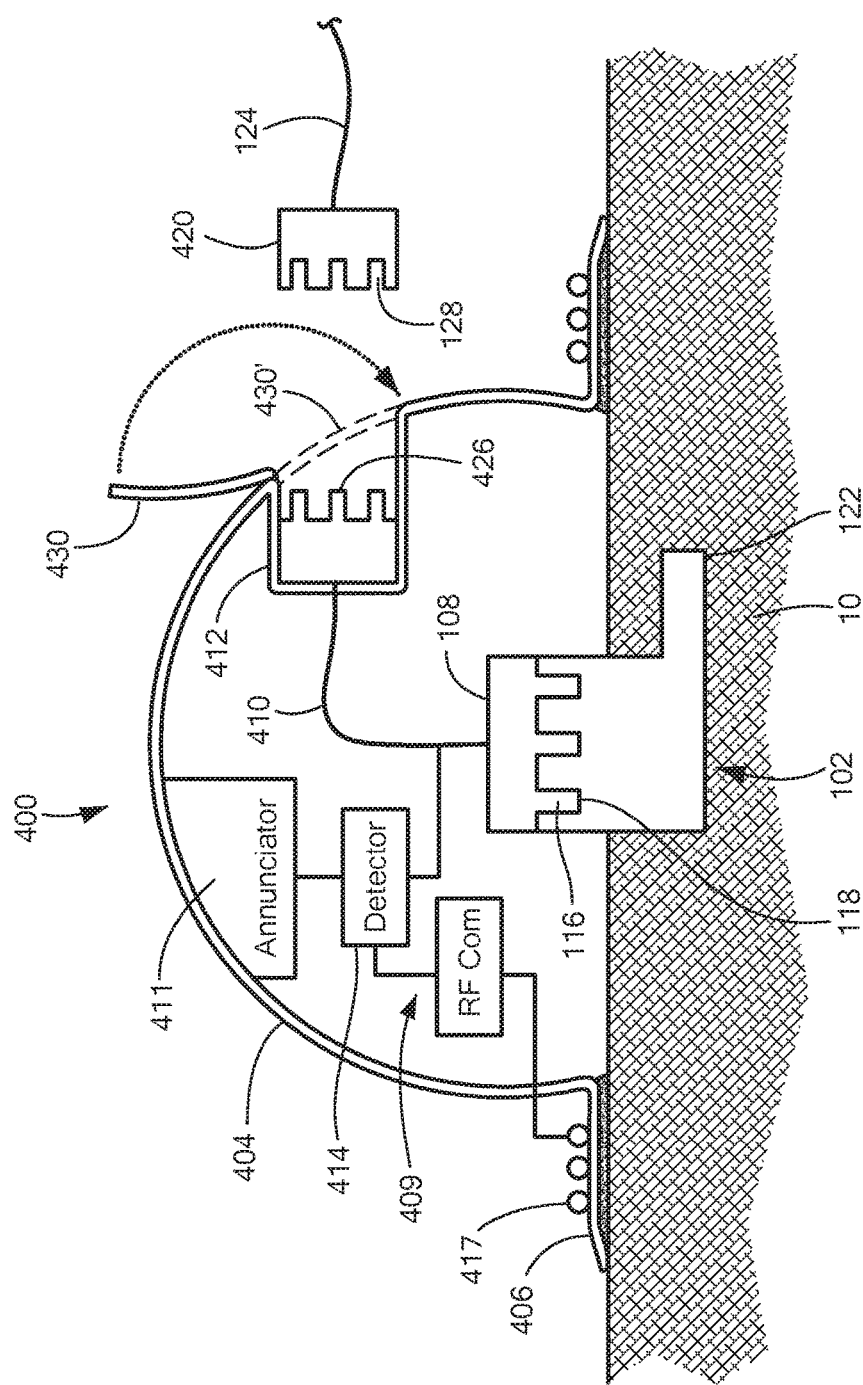
FIG. 4 is a view similar to FIG. 2 but depicting a cover according to another embodiment of the disclosure.

Referring now to FIG. 4, cover 400 is similar to the cover 100 discussed above, except as noted below. In cover 400, the second connector 412 has a configuration different from the percutaneous connector 102. The connector 420 of the external device is configured to mate with the second connector, and cannot be connected directly to the percutaneous connector. Also, in this embodiment, the second connector 412 is located completely in a recess formed in the outer side of the structure, such as a depression in housing 404. The depression can be temporarily covered by a closure 430. In this embodiment, the closure 430 is attached to the housing 404, and can be moved from the open position depicted in solid lines in FIG. 5 and the closed position depicted in broken lines at 430'. When the closure 430 is in open position, the second connector 412 is exposed to the outside of the structure. In a further variant, closure 430 can be replaced by a self-sealing membrane (not shown) that can be penetrated by the mating elements of the connectors. In a further variant, the closure can be a separate cap, not attached to the housing.

The cover of FIG. 4 may further include an alarm circuit 409 mounted to the structure. The alarm circuit is operatively connected to one or both of the connectors so that the alarm circuit can detect a condition prevailing in the circuit including one or more of the contacts of the connectors, and to determine when the condition deviates from limits. In FIG. 4, this connection is shown schematically as a branching of the cable extending between the conductors. However, the connection need not be a conductive connection. For example, the alarm circuit can be inductively or capacitively coupled to one or more of the contacts of the connectors or to one or more conductors of the cable. The alarm circuit can be arranged to detect current or voltage prevailing in the circuit incorporating the connectors through a detector 414, or to receive signals passed through the circuit by the internal or external device. The alarm circuit typically includes a source of power such as a small battery (not shown) and may be arranged to draw power from the circuit including the connectors as, for example, to charge the alarm circuit battery using some of the power delivered by the external device while the external device is connected. The alarm circuit includes an annunciator 411 mounted in the cover 400. The annunciator 411 is arranged to emit an alarm signal in a human-perceptible form responsive to the determination that the condition deviates from limits. For example, the annunciator can include elements such as a light-emitting device for providing a visible signal; a buzzer for emitting an audible signal; or a vibrator for emitting a tactile signal that can be detected by the patient. In this embodiment, the alarm circuit also includes a radiofrequency ("RF") transmitter for sending the alarm signal by wireless communication to a receiver (not shown) by means of an antennae 417 located on a base 406 of the cover 400. Typically, the external device includes a patient interface that provides alarm signals. In some cases, the alarm signal provides detailed information about the nature of the problem as, for example, text or an icon specific to the particular problem detected. When the external device is disconnected from the internal device, the alarm function typically is disabled. The alarm signal provided by the cover can alleviates this drawback. It is not necessary for the alarm signal provided by the cover to provide detailed information about the nature of the problem; the alarm signal may simply tell the patient or medical personnel that the external device should be reconnected to provide more detailed information.

Figure 5:
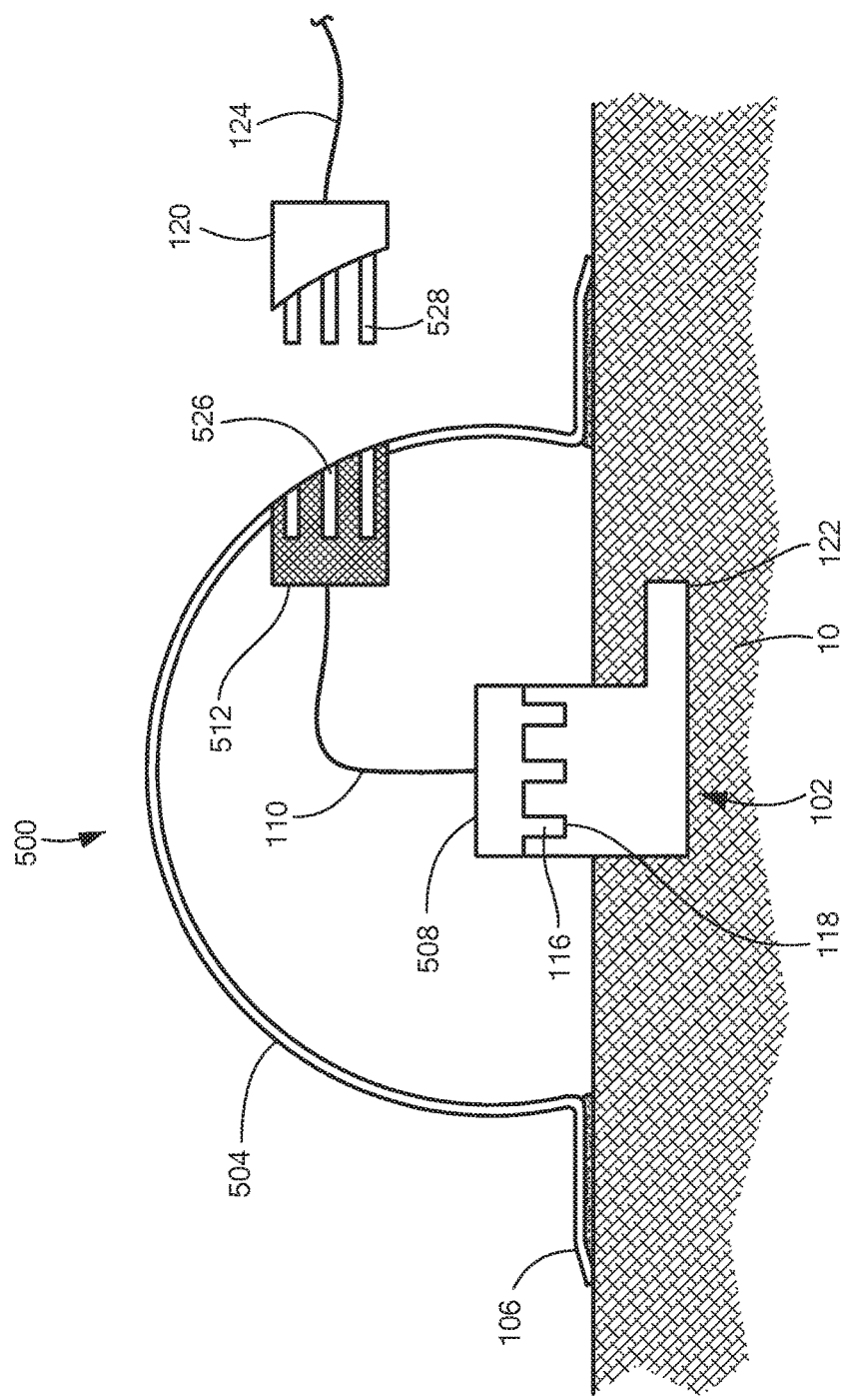
FIG. 5 is a diagrammatic cross-sectional view along the center line of yet another embodiment of a cover.

FIG. 5 shows a cross-sectional view of yet another embodiment of a cover 500. Cover 500 is similar to the covers discussed above except as specifically mentioned. In cover 500, the second separable connector 512 is different from the first separable connector 508. The outer exposed surface of the second separable connector 512 is contoured to match a dome-shaped central housing structure 504. In this embodiment, the second separable connector has a set of base contacts 526 to mate with a set of cap contacts 528 present on the external device connector. The base contacts 526 are shaped to align with the profile of the central housing structure, and consequently render a smooth exterior cap surface with no protrusions when the external device is disconnected from the cover.

In the embodiments discussed above, the elements constituting the cover are permanently attached to one another, so that the entire cover is handled and placed as a unit. However, this is not essential. For example, in the embodiment discussed above with reference to FIGS. 1 and 2, the central housing 104, connectors and cable may form one unit, whereas the base 106 may be provided as a separate element as, for example, a ring cut from a flexible adhesive-coated sheet. Such a separate element can be attached to the central housing during manufacture, or during placement of the cover on the patient. Furthermore, the central housing structure may have different shapes and may only partially cover the percutaneous connector in other embodiments not shown here.

Figure 6:
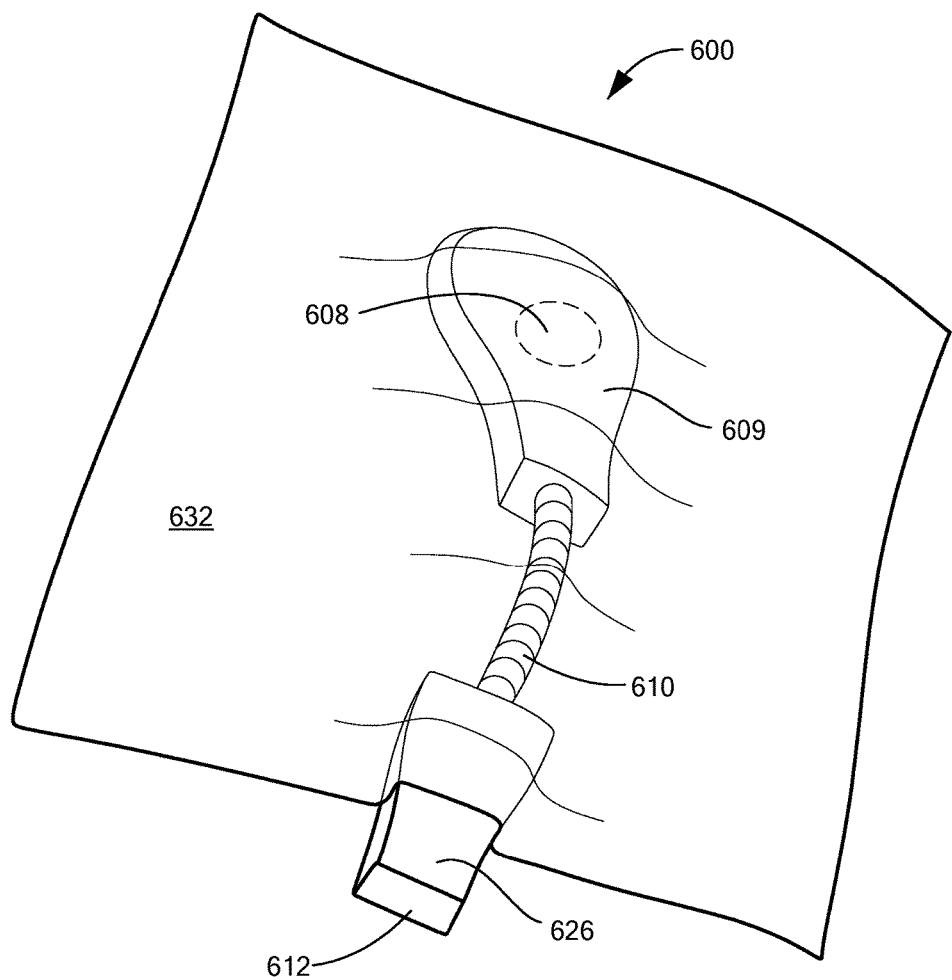
FIG. 6 is a diagrammatic perspective view of a still yet another embodiment of a cover.

FIG. 6 shows a perspective view of still yet another embodiment of a cover 600. In this embodiment, the structure includes a first separable connector 608 matable with a percutaneous connector and having a first connector body 609. A second separable connector 612 for connection with an external device connector has a second connector body 626. A flexible cable permanently connects the first and second connectors with one another to form a unit. The structure of the cover 600 further includes a flexible, adhesive-bearing sheet 632. Either during manufacture or during installation on a patient, cover 632 is overlaid across this unit so that the sheet 632 overlies first connector body 609 and cable 610, and overlies a part of the second connector body 626, leaving the mating elements of the second connector 612 projecting beyond the sheet. Here again, the second connector is exposed at the outside of the cover when the cover is in place on the patient. The sheet 632 secures and anchors the first connector and the electrical conduit 610 to the adjacent skin, and allows access to the second separable connector 612. This arrangement ensures that manipulating the second separable connector to connect and disconnect to an external device will not disturb the first connector or the electrical cable. In other embodiments, the overlaying cover may only cover the first housing and partially cover the electrical conduit leaving the second separable connector unsecured.

The embodiments discussed above can be further varied. For example, the included in the covers discussed above, such as central housing 101 the shown in FIGS. 1 and 2, need not be a molded element, but can instead be formed from a woven fabric material or any other material that will allow the cover to be worn for extended periods of time. Also, the first and second separable connectors need not be formed with separate bodies. For example, two separable connectors may be formed at opposite ends of a common connector body. The particular percutaneous connector, and the particular designs of the separable connectors discussed above, are merely exemplary. The covers discussed herein may incorporate different types of separable connectors adapted to mate with any type of percutaneous connector and with any type of external device connector. As mentioned above, the cover desirably is disposable. By contrast, the percutaneous connector and the connector of the external device typically are designed for long service life and many repeated interconnections. The first and second separable connectors incorporated in the cover may be less expensive connectors that are compatible with the percutaneous connector and with the connector of the external device, respectively.

Figure 8:
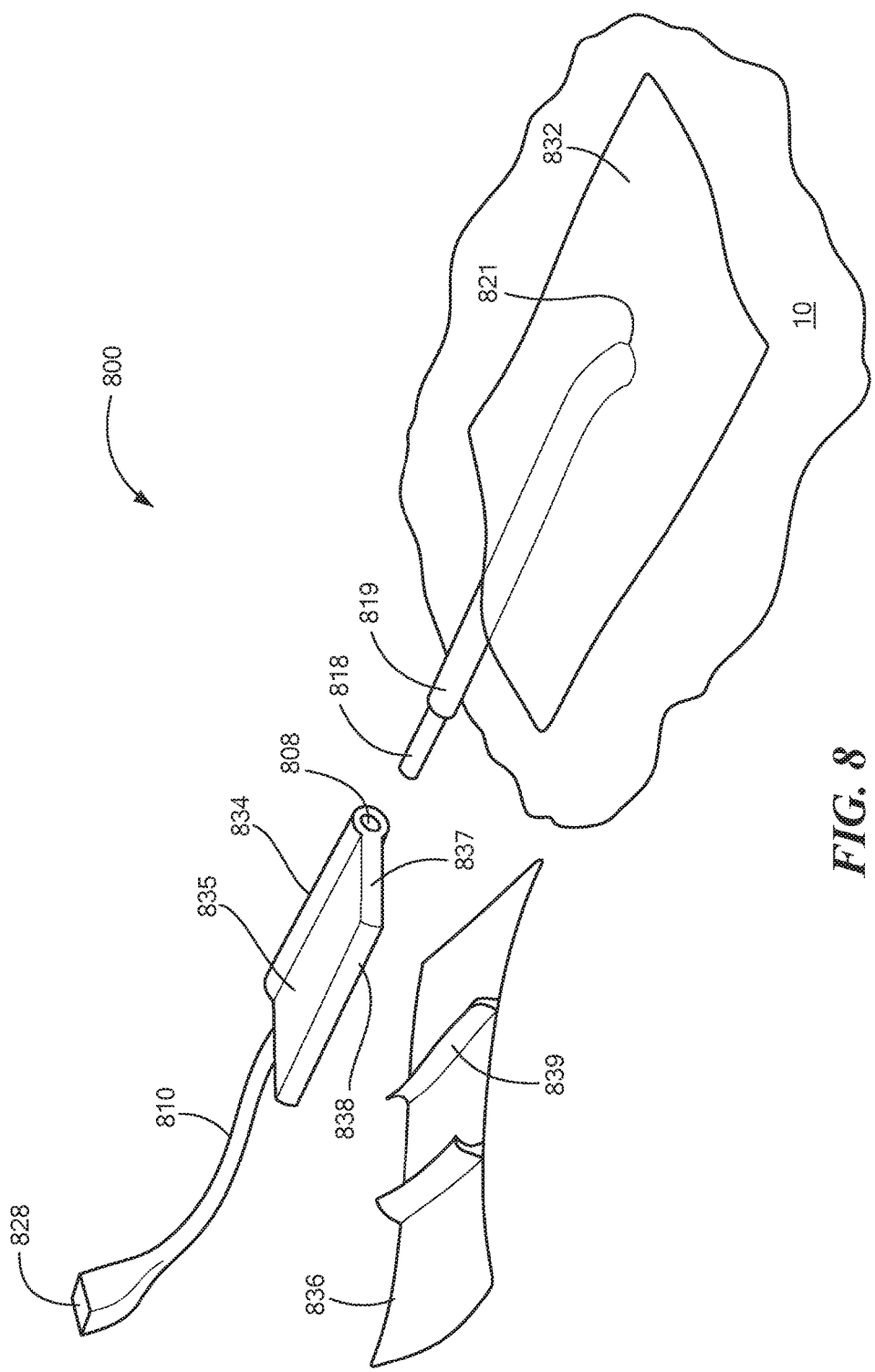
FIG. 8 is a diagrammatic perspective view of a detachable device according to one embodiment of the present disclosure in conjunction with a percutaneous cable.

FIG. 8 shows a detachable device 800 that can be directly connected to a percutaneous cable 819 extending from the skin. In this embodiment, a percutaneous cable configured to traverse through a patient's skin is used as the percutaneous element instead of a percutaneous connector. The percutaneous cable 819 extends through the skin at a skin breach location 821. Detachable device 800 includes a structure having a pod or housing 834 with a female separable connector 808. In this embodiment, the pod is generally in the form of a rectangular solid having a top surface 835, facing upwardly in FIG. 8, a bottom surface 838 facing oppositely from the top surface, and edge surfaces 837 extending between the top surfaces. The pod desirably has a thickness between its top and bottom surfaces that is less than its length and width. A female separable connector is mounted within the pod and has an opening in one of the edge surfaces 837. A male separable connector 818 of percutaneous cable 819 can be inserted into female separable connector 808 to electrically connect the cable to the female separable connector 808 and mechanically connect the cable to the pod. In this embodiment, the connection between the male connector 818 and female connector 808 is arranged so the connection is substantially fluid-tight and resistant to accidental disconnection. As discussed below, the connection with the percutaneous cable is intended to remain connected unless and until it is deliberately disconnected by a caregiver such as a nurse or a physician. For example, the male connector 818 and female connector 808 may be as described in U.S. patent application Ser. No. 14/971,311, the disclosure of which is hereby incorporated by reference herein and a copy of which is annexed hereto as a part of this disclosure.

Figure 9:
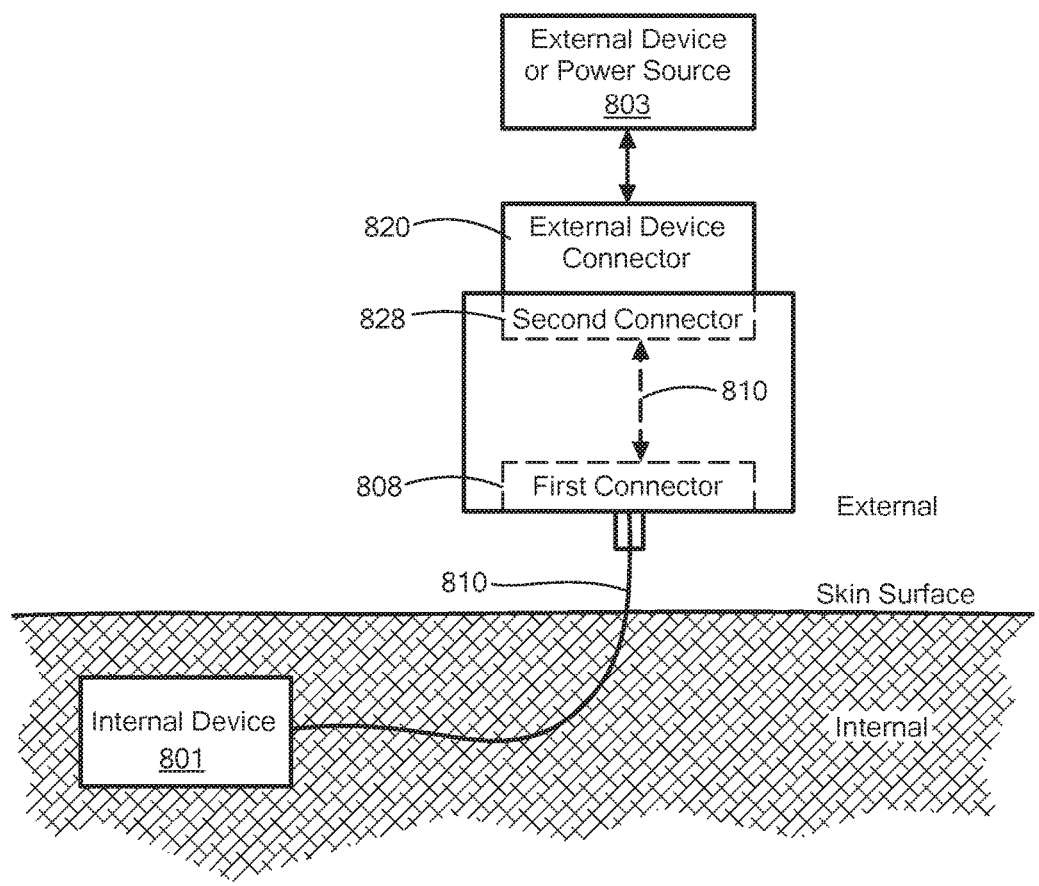
FIG. 9 is a schematic drawing of a circuit between an internal device and external device connected through a percutaneous cable.

A second separable connector 828 is attached to pod 834 by a cable 810. As shown in FIG. 9, the second separable connector interfaces with an external device or a power source to complete the connection with the internal device. In other embodiments, the second separable connector may be contained within the pod. The second separable connector in this embodiment is configured as a breakaway connector, adapted to release its connection to a connected device in response to a pull on the connected device or on cable 810.

The structure of device 800 further includes an anchor 836 adapted to secure pod 834 to the surface of the skin. Anchor 836 includes a sheet with an adhesive on its skin-facing surface that can be attached to the skin. The opposite side of anchor 836 is configured to securely hold pod 834 against movement relative to the adhesive sheet 836. In this embodiment, anchor 836 has a clip 839 adapted to releasably engage the exterior of pod 834. In other embodiments, the anchor may include features such as projections on the anchor that engage in holes in the pod or vice-versa, hook and loop fasteners such as those sold under the trademark VELCRO on the pod and on the anchor, threaded fasteners, and other mechanical fasteners. In other embodiments, adhesives may be employed. The secure but releasable connection between the pod and the anchor allows anchor 836 to transmit mechanical loads imposed on pod 834 to the attached skin, thereby insulating the percutaneous cable 819 from mechanical loads. A standard wound dressing 832, separate from anchor 836 secures and protects percutaneous cable 819 and the skin breach location. This dressing typically includes a flexible, adhesive-bearing sheet. Pod 834 may also include an alarm circuit to detect a condition prevailing in the circuit as more fully described above in the description of percutaneous cover 400. Pod 834 can be water-proof, to allow patients to shower or swim with the pod after detaching from the external device. Also, as more fully described above in the method to attach percutaneous cover 400, detachable device 800 can similarly be attached to percutaneous cable 819. Anchor 836, pod 834 and sheet 832 are configured to be disposable, and may be replaced at suitable intervals.

The method of using device 800 is generally similar to the methods discussed above. With the percutaneous cable in place and preferably already secured at the skin breach site by dressing 832, the connector 818 of the percutaneous cable is connected to the first separable connector 808 of the device, and the structure of the device is secured to the skin of the patient at a site remote from the skin breach site using anchor 836 to secure pod 834 in place. For example, the pod may be placed a few cm from the skin breach site, so that only a short length of the percutaneous cable extends outside of the patient's body in proximity to the skin. Some or all of this length is covered by dressing 832, and additional dressings may be used if complete coverage is desired. Typically, these steps are performed by a trained caregiver. The connector 820 of the external device (FIG. 9) is connected to the second separable connector, to form the completed circuit between the external device 803 and the internal device 801. As discussed above, the patient may temporarily disconnect and reconnect the external device connector.

Anchor 836 may be replaced without replacing pod 834 and without breaking the connection between the percutaneous cable 819 and the first separable connector on the pod. The patient or a trained caregiver may release the connection between pod 834 and anchor 836, peel anchor 836 away from the skin, place a new anchor at the same or a different location on the skin, and attach the pod to the new anchor. During this procedure, care should be taken to avoid disturbing that portion of percutaneous cable that extends through the skin breach site. For example, the caregiver can hold the cable between the pod and the skin breach site. Dressing 832 helps to hold the cable during this procedure. Because only the anchor is discarded in this procedure, the anchor can be changed frequently at minimal cost. With repeated connection and disconnection of the external device connector, the second separable connector 828 may become damaged. In that event, the caregiver can release the connection between the male connector 818 (FIG. 8) and the first separable connector 808, remove the pod 834, cable 810 and second connector 828 as a unit replace it with a new unit, using the same or a different anchor 836. Here again, failure of the second connector does not require a surgical procedure to replace the percutaneous element, i.e., percutaneous cable 818. Because the first connector 808 and male connector 818 are subjected to only infrequent connections and disconnections, these elements can provide reliable service for many years.

The structure of device 800 described above can be varied in many ways. In one variant, the second connector 828 is mounted directly to the pod 834, so that cable 810 is omitted. In another variant, the pod 834 is omitted and replaced by a short cable (not shown) having the first connector 818 at one end and the second connector 828 at the opposite end. Here again, the anchor 836 is arranged to hold the short cable in place. In yet another variant, anchor 836 may be permanently fastened to the pod or cable having the first and second connectors. In a still further variant, the anchor may be a simple adhesive sheet that is secured both to the patient's skin and to the pod or short cable by the adhesive on the sheet.

Although the invention herein has been described with reference to particular embodiments, it is to be understood that these embodiments are merely illustrative of the principles and applications of the present invention.

What is claimed is:

1. A cover for a percutaneous connector extending through the skin of a patient comprising:
    an enclosure having an inner side and an outer side and defining a depression;
    a first separable connector mounted to the enclosure and disposed entirely within the enclosure, the first separable connector being configured to detachably engage and electrically connect with the percutaneous connector, the enclosure being configured to isolate a distal end of the percutaneous connector from an exterior of the enclosure;
    a second separable connector mounted to the enclosure and disposed within the depression, the second separable connector being electrically connected to the first separable connector, the second separable connector being exposed at the outer side of the enclosure and being configured to detachably engage and electrically connect with an external device, the second separable connector being spaced apart from the first connector by a cable; and
    the inner side of the enclosure defining a skin-engaging surface at least partially surrounding the first separable connector and the percutaneous connector, when the first separable connector is engaged with the percutaneous connector.

2. The cover of claim 1, wherein the skin-engaging surface extends entirely around the first separable connector.

3. The cover of claim 1, further comprising an adhesive on the skin-engaging surface.

4. The cover of claim 1, wherein the enclosure includes a housing and a flexible base extending beyond a periphery of the housing, the flexible base defining at least a portion of the skin-engaging surface.

5. The cover of claim 4, wherein the base is integral with the housing.

6. The cover of claim 4, wherein the second separable connector is disposed in a second housing and connected to the first separable connector by an electrical conduit, the second separable connector being accessible to connect with an external device and manipulation of the second separable connector does not interfere with the connection between the first separable connector and the percutaneous connector when the cover is disposed over the first separable connector and the first separable connector is engage with the percutaneous connector.

7. The cover of claim 1, further comprising a closure configured to releasably engage at least one from the group consisting of the enclosure and the second separable connector, the closure being configured to cover the second separable connector when the external device connection is absent.

8. The cover of claim 1, further comprising an alarm mounted to the enclosure and electrically connected to at least one from the group consisting of the first separable connection and the second separable connector, the alarm being configured to emit an alarm signal responsive to an electrical condition prevailing at the at least one from the group consisting of the first separable connection and the second separable connector.

9. The cover of claim 8, wherein the alarm signal includes at least one from the group consisting of an audio, tactile, and visual alarm.

10. A method of providing a connection between an external device and an internal device implanted in a patient and electrically connected through a percutaneous connection element across a skin surface of the patient, the method comprising:
    coupling a first separable connector to the to the percutaneous connection element;
    securing the first separable connector to the skin surface independent of the engagement between the first separable connector and the percutaneous connection element, the first separable connector being spaced apart and electrically connected to a second separable connector exposed outside of the patient, the first connector being coupled to a cover, and the second connector being disposed within a depression defined by the cover, the cover being configured to enclose and isolate a distal end of the percutaneous connection element from an external environment; and
    connecting the external device to the second separable connector.

11. The method of claim 10, further comprising detaching the external device from the second separable connector.

12. The method of claim 11, further comprising removing the first and second separable connectors.

13. The method of claim 10, wherein securing the first separable connector includes applying an adhesive-bearing element to the skin of the patient, and wherein the adhesive-bearing element holds the first separable connector in place.

14. The method of claim 13, wherein the percutaneous connection element is a percutaneous connector extending through the skin, and wherein application of the adhesive-bearing element covers the percutaneous connector and protects the percutaneous connector from microbes.

15. The method of claim 13, wherein applying the adhesive-bearing element includes applying the cover including the first separable connector and the adhesive-bearing element.

16. The method of claim 15, further comprising operating an alarm circuit mounted to the cover and electrically connected to at least one of from the group consisting of the first separable connector and the second separable connector, the alarm circuit being configured to detect an electrical condition representing a condition of the internal device and emit an alarm signal responsive to such condition.

17. The method of claim 10, wherein the percutaneous connection element is a percutaneous cable extending through the skin surface of the patient.

18. The method of claim 17, wherein the first separable connector is secured to the skin remote from a skin breach location where the percutaneous cable extends through the skin.

19. A cover for a percutaneous connector extending through the skin of a patient comprising:
- a housing defining a substantially dome shape and a base surrounding the housing and extending beyond the periphery of the housing, the housing isolating a distal end of the percutaneous connector from an external environment;
- a first separable connector mounted to the structure and disposed entirely within the housing, the first separable connector being configured to detachably engage and electrically connect with the percutaneous connector; and
- a second separable connector entirely mounted within a depression defined by the dome and electrically connected to and spaced part from the first separable connector, the second separable connector being exposed at the outer side of the dome and being configured to detachably engage and electrically connect with an external device,
- the inner side of the base defining a skin-engaging surface surrounding and enclosing the first separable connector and the percutaneous connector when the first separable connector is engaged with the percutaneous connector, the inner side including an adhesive on the skin-engaging surface.

* * * * *